US008465514B1

(12) United States Patent
Rose

(10) Patent No.: US 8,465,514 B1
(45) Date of Patent: Jun. 18, 2013

(54) TOURNIQUET SYSTEM

(75) Inventor: Keith J. Rose, Corpus Christi, TX (US)

(73) Assignee: Alliant Techsystems Inc., Minneapolis, MN (US)

( * ) Notice: Subject to any disclaimer, the term of this patent is extended or adjusted under 35 U.S.C. 154(b) by 0 days.

(21) Appl. No.: 13/175,430

(22) Filed: Jul. 1, 2011

Related U.S. Application Data

(63) Continuation-in-part of application No. 11/599,980, filed on Nov. 15, 2006, now abandoned.

(51) Int. Cl.
*A61B 17/00* (2006.01)

(52) U.S. Cl.
USPC ......................................................... 606/203

(58) Field of Classification Search
USPC ..................... 2/87, 201, 202, 243.1; 606/151, 606/157, 158, 191, 192, 194, 201–203
See application file for complete search history.

(56) References Cited

U.S. PATENT DOCUMENTS

| | | | |
|---|---|---|---|
| 2,387,428 A | 10/1945 | Brothers | |
| 2,480,430 A | 8/1949 | Walters | |
| 2,702,551 A | 2/1955 | Hobson | |
| 3,969,772 A | 7/1976 | Pravaz | |
| 6,852,089 B2 | 2/2005 | Kloecker et al. | |
| 7,604,651 B1 | 10/2009 | Harris et al. | |
| 2003/0036771 A1 | 2/2003 | McEwen et al. | |
| 2005/0240217 A1 | 10/2005 | Jennifer et al. | |
| 2005/0273134 A1 | 12/2005 | Esposito | |
| 2007/0299467 A1 | 12/2007 | Arias | |

*Primary Examiner* — Ryan Severson
*Assistant Examiner* — Ashley Cronin
(74) *Attorney, Agent, or Firm* — Wooten & Shaddock, PLC

(57) ABSTRACT

A tourniquet system, having at least one circumferential enclosed channel formed in a garment; a tourniquet band positioned in the at least one circumferential enclosed channel; a tightening and securing mechanism associated with the tourniquet band, wherein the tightening and securing mechanism includes two or more apertures formed therethrough, and wherein at least a portion of the tourniquet band loops through the apertures of the tightening and securing mechanism, such that when the tightening and securing mechanism is turned, a diameter of the tourniquet band is decreased and a tourniquet force is applied to an inside wall of the circumferential enclosed channel; and at least one portal in the garment, proximate the circumferential enclosed channel, to provide access to the tightening and securing mechanism.

14 Claims, 7 Drawing Sheets

TOURNIQUET SYSTEM

CROSS-REFERENCE TO RELATED APPLICATIONS

This nonprovisional patent application is a Continuation-in-Part of U.S. patent application Ser. No. 11/599,980, filed Nov. 15, 2006, the disclosure of which is incorporated herein by reference in its entirety.

BACKGROUND OF THE INVENTION

1. Field of the Invention

The present invention is directed generally to tourniquets. In particular, the present invention relates to a tourniquet system having a tourniquet band and an anti-pinch plate. The present invention also relates to various garments that may be used in conjunction with the tourniquet system.

2. Description of Related Art

A tourniquet is generally a tightly tied band applied around a body part (for example, a bandage tightened around an arm or a leg by twisting) in an attempt to arrest bleeding by forcibly compressing a blood vessel. A tourniquet is typically applied as a last resort method when bleeding cannot be controlled through alternative methods and the amount of blood loss is likely to cause death in seconds to minutes.

Because the application of a tourniquet stops the flow of blood to the portion of the limb below the level where the tourniquet is applied, the resulting anoxia can cause the death of at least a portion of the limb, often requiring the later surgical amputation of the limb just below the level the tourniquet is applied. This is likely to occur when the tourniquet stays in place several hours.

The decision to employ a tourniquet should be made by an emergency medical technician or preferably a doctor if possible. However, when severe external bleeding cannot be controlled by other means, and a tourniquet may be the only way to save the life of an injured individual, time constraints might require the decision to be made by the injured party himself.

On the modern battlefield, for example, life-threatening bleeding from injuries to extremities is more common because modern body armor tends to protect the torso from such wounds. Blast injuries to limbs rarely result in a clean amputation or a salvageable limb, and rapid application of a tourniquet can be lifesaving when arterial bleeding results from such a major injury.

It is believed that approximately 70% of all preventable fatalities on the modern battlefield are the result of extremity trauma. Unfortunately, medical care is not always immediately available and an injured individual or someone within close proximity has to tend to their own or their friend's wounds. This has been particularly true where use of improvised explosive devices has sharply increased. The users have armor that protects their torsos and to a lesser degree their heads; however, since the extremities are left unprotected the users are more likely to suffer a severe laceration in those extremities. The large loss of blood from these lacerations can be avoided with the quick application of a well-placed tourniquet.

It has been noted that tourniquets are used far more frequently in combat injury situations. Therefore, most military personnel are now required to carry a tourniquet as part of their individual first aid kits, and first aid training for soldiers now typically addresses the "prompt and decisive" use of tourniquets to control life-threatening extremity bleeding.

BRIEF SUMMARY OF THE INVENTION

However, known tourniquets merely include a band and a bar. When the tourniquet is applied, the band is positioned around an injured arm or leg, at a position above the injury. Once the band is in position, a separate bar is placed between the band and the extremity and the bar is rotated. As the bar is rotated, the band is twisted, thereby reducing the circumference of the band and tightening the band so as to forcibly compress the extremity (and the blood vessels within the extremity) and reduce or eliminate blood flow below the level where the tourniquet is applied.

Additionally, because of the degree of personalization that occurs within each individual soldier's kits, a carried tourniquet's location on a soldier can vary greatly from individual to individual causing a fellow soldier or attending Medical Aide to take even more time in the complete application cycle or effort.

In some instances, a carried tourniquet can become separated from the injured soldier causing him, her, or an attending Medical Aide to expend valuable time attempting to locate the tourniquet rather than applying it.

In certain situations, the injured, weakened, user may have to apply the tourniquet himself or herself. Unfortunately, particularly in a stressful situation, it may be difficult to locate, apply, properly position, or effectively utilize a tourniquet.

Additionally, known tourniquets are often carried in the field by someone else, such as a dedicated Medical Aide, or by the potential user in a pouch or pack. The time lost in accessing the tourniquet and/or positioning it could be life threatening. In some cases, the injury and/or the position of the wounded individual might prevent the tourniquet from being accessed and positioned at all.

The present invention in its several disclosed embodiments alleviates the drawbacks described above with respect to the current methods and systems for dealing with severe lacerations and incorporates several additional beneficial features. The general objective of the present invention is to provide a new and improved tourniquet system that can be incorporated into a garment. The garment may be an article of clothing or may be a specialized uniform or suit, such as a pilot's pressurized suit or a wet suit. The garment may be a protective covering worn over conventional clothing.

Unfortunately, medical care is not always immediately available and the user or his buddy may be forced to tend to his own or his friend's wounds. The large loss of blood from severe lacerations, for example, can be avoided with the quick application of a well-placed tourniquet.

In some situations, as described above, an injured, weakened user may have to apply the tourniquet himself and the tourniquet system of the present invention can be incorporated into one or more garments to place one or more tourniquets in particular locations such that the least amount of pressure is required to arrest the largest amount of blood flow. On the upper extremities, the first tourniquet band's centerline must lie proximal to the superior position of the bicep and the second tourniquet band's centerline, on the same upper extremity, must be within about two centimeters below the elbow of the wearer. On the lower extremities, the first tourniquet band's centerline must lie within about two centimeters distal to the inguinal crease and the second tourniquet band's centerline must lie two centimeters distal to the tibial tuberosity.

The invention would add a much-needed medical supply to each user's garment without sacrificing the comfort of the user, the weight of the garment, or the user's ability to move through his environment stealthily. The tourniquet is positioned inside the garment such that it will be in the optimal position for use and the webbing used to maintain the position of the tourniquet is light, and non-chafing. The tourniquet itself is made with tactical-grade nylon or a similar material and is positioned between the webbing and the interior of the garment. The tightening and locking mechanism is made of a lightweight metal or durable polymer or similar material and placed below the flap of the garment for easy access. The flap also acts to protect the tourniquet during times of disuse and acts maintain a smooth appearance to the user's garment.

While the tourniquet system of the present invention may be designed to function as a stand-alone system, in various exemplary, nonlimiting embodiments, the tourniquet system of the present invention may be incorporated into or included as an integral component of a garment. In these exemplary embodiments, the tourniquet system of the present invention may be incorporated into a more traditional garment, such as, for example, a pair of pants, a shirt, or a jacket. Additionally, the tourniquet system may also be incorporated into other traditional or non-traditional garment, such as, for example, a harness, body-fitting framework, suspension system, Long John type configuration, bicycle type or exercise shorts, compression short or shirt, wetsuits, sky diving garments, hazmat suits, pressurized suits, flight suits, hunting apparel, overalls, coveralls, specialized uniforms or suits, protective coverings worn over conventional clothing, and/or any other garment, quasi-garment, or article of clothing that is capable of maintaining one or more tourniquets in a relatively fixed position relative to the body of a wearer.

For example, the tourniquet system of the present invention may be incorporated into wetsuits for implementation after shark attacks, sky diving garments to be worn by individuals being dropped into an area not easily accessible by ground, or hazmat suits where the user might be in contaminated conditions that cannot be readily entered by supporting trauma personnel. Variants could also include a pneumatic tourniquet that the wearer could trigger to apply increasing compressing pressure at a desired tourniquet location without any manual force or an attached transmitter that would activate when the tourniquet system is used to alert the medical field to the user's location and particular injury.

An object of this invention is to provide a garment having a total of eight tourniquets incorporated into the inner surface of the garment with webbing that is non-chafing and light; an object of this invention is to have tourniquets incorporated into the inner surface of the garment at strategic locations requiring the least amount of pressure applied to result in the lowest amount of blood loss from the extremity; an object of this invention is to provide a garment having tourniquets incorporated into the inner surface of the garment with flaps available at the site of each tourniquet's tightening and securing mechanism in order to allow for easy access to the tourniquet, to protect the tightening and securing mechanism from the environment during non-use and to maintain the smooth appearance of the user's garment. An object of this invention is to provide a garment with an additional lever or bar, while continuing to maintain the smooth appearance of the user's garment, to allow additional torque to be applied by the injured user or second party if necessary.

The present invention will be more clearly understood from the following description of illustrative embodiments thereof, to be read by way of example and not of limitation in conjunction with the apparatus and the method described.

The beneficial effects described above apply generally to the examples disclosed herein of the tourniquet system. The specific components and configurations through which these benefits are delivered will be described in detail herein below.

In certain exemplary, nonlimiting embodiments, the tourniquet system of the present invention includes a tourniquet band and a tightening and securing mechanism associated with the tourniquet band, wherein the tightening and securing mechanism includes two or more apertures formed therethrough, and wherein at least a portion of the tourniquet band loops through the apertures of the tightening and securing mechanism, such that when the tightening and securing mechanism is turned, a diameter of the tourniquet band is decreased.

In other exemplary, nonlimiting embodiments, the tourniquet system of the present invention includes at least one circumferential enclosed channel formed in a garment; a tourniquet band positioned in the at least one circumferential enclosed channel; a tightening and securing mechanism associated with the tourniquet band, wherein the tightening and securing mechanism includes two or more apertures formed therethrough, and wherein at least a portion of the tourniquet band loops through the apertures of the tightening and securing mechanism, such that when the tightening and securing mechanism is turned, a diameter of the tourniquet band is decreased and a tourniquet force is applied to an inside wall of the circumferential enclosed channel; and at least one portal in the garment, proximate the circumferential enclosed channel, to provide access to the tightening and securing mechanism.

The tightening and securing mechanism extends from a first end to a second end and, in certain exemplary embodiments, the tightening and securing mechanism is substantially curved over its length. Alternatively, the tightening and securing mechanism is substantially planar over its length. Generally, the two or more apertures are formed proximate a center of the tightening and securing mechanism.

Accordingly, this invention provides a tourniquet system, which includes an integral tightening and securing mechanism that operates as both a buckle and a windless or bar.

This invention separately provides a tourniquet system, which is made up of a reduced number of components.

This invention separately provides a tourniquet system, which is capable of being Incorporated into a garment.

These and other features and advantages of this invention are described in or are apparent from the following detailed description of the exemplary, nonlimiting embodiments.

BRIEF DESCRIPTION OF THE DRAWINGS

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a basis for the claims and as a representative basis for teaching one skilled in the art to employ the present invention.

The exemplary embodiments of this invention will be described in detail, with reference to the following figures, wherein like reference numerals refer to like parts throughout the several views, and wherein.

DETAILED DESCRIPTION OF EXEMPLARY EMBODIMENTS

Figure 1:
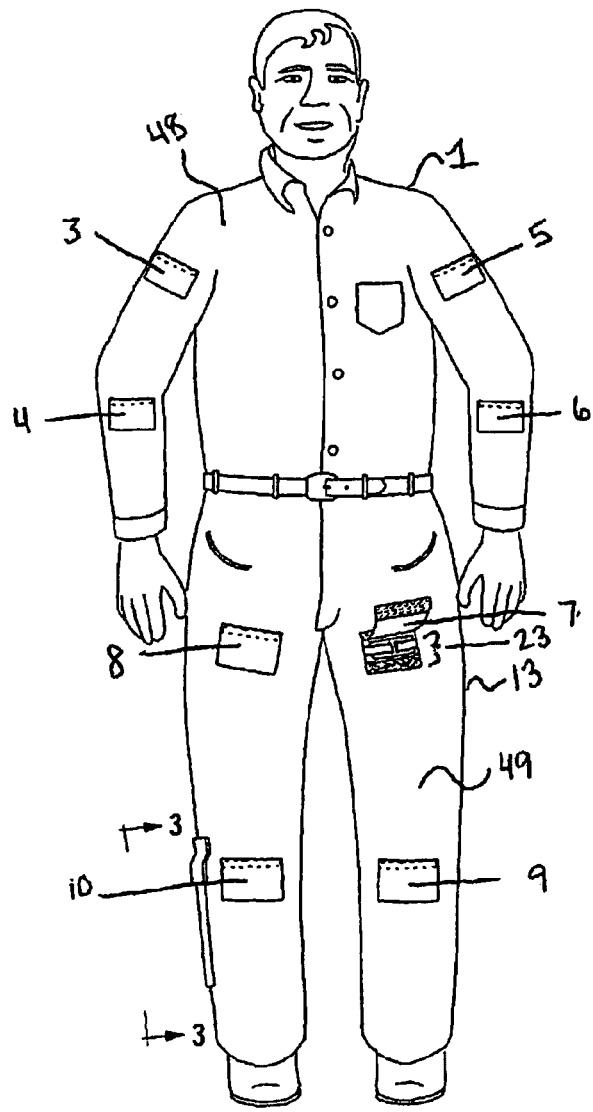
FIG. 1 shows a perspective view disclosing an exemplary embodiment of the tourniquet system formed in accordance with the present invention.

For simplicity and clarification, the design factors and operating principles of the tourniquet system according to this invention is explained with reference to various exemplary embodiments of a tourniquet system. The basic explanation of the design factors and operating principles of the tourniquet system is applicable for the understanding, design, and operation of the tourniquet system of this invention.

Furthermore, it should be appreciated that, for simplicity and clarification, the embodiments of this invention will be described with reference to the tourniquet system being included as a part of a tourniquet system. However, it should be appreciated that the tourniquet system of this invention may be incorporated into any garment or covering, such as, for example, a shirt, pair of pants, pair of shorts, flight suit, swimsuit, wetsuit, uniform, battlefield outerwear, fire fighter outerwear, police outerwear, or the like.

It should also be appreciated that the terms "tourniquet" and "tourniquet system" are used for basic explanation and understanding of the operation of the systems, methods, and apparatuses of this invention. Therefore, the terms "tourniquet" and "tourniquet system" are not to be construed as limiting the systems, methods, apparatuses, or applications of this invention.

Likewise, it should also be appreciated that, as used herein, the term "garment" is used for basic explanation and understanding of the operation of the systems, methods, and apparatuses of this invention. Therefore, the term "garment" is not to be construed as limiting the systems, methods, and apparatuses of this invention. Thus, the term "garment" is to be understood to broadly include any complete or partial article of clothing that is capable of maintaining one or more tourniquets in a relatively fixed position relative to the body of a wearer. For example, the term "garment" is to be understood to broadly include any shirt, pants, jacket, harness, body-fitting framework, suspension system, Long John type configuration, bicycle type or exercise short, compression short or shirt, wetsuit, sky diving garment, hazmat suit, pressurized suit, flight suit, hunting apparel, overalls, coveralls, specialized uniform or suit, protective covering, and/or any other traditional or non-traditional garment, quasi-garment, or the like.

While the attached drawing figures illustrate an exemplary tourniquet system integral to a pair of pants and a shirt, it should be appreciated that the tourniquet system may be utilized alone or in conjunction with any garment, as provided for herein. Likewise, it should be appreciated that any known or later developed tourniquet system may be utilized in conjunction with the pants or shirt illustrated in the attached drawing figures or any other garment incorporating the features of the present invention. Thus, it should be understood that the tourniquet system, pants, and shirt illustrated herein are merely for exemplary purposes and the tourniquet system and/or garments could be of other types.

Turning now to the drawing figures, FIGS. 1 through 14 illustrate certain exemplary embodiments of the tourniquet system 100 of the current invention. FIG. 1 depicts a first exemplary embodiment of the tourniquet system 100 in a garment that comprises a full-sleeved, button-down shirt 1 with exterior surface 48 and two-pocket pants 13 with exterior surface 49. It is understood that the shirt 1 is merely for exemplary purposes and the garment could be of other types, as discussed above.

The shirt 1 and pants 13 optionally include eight flaps 3, 4, 5, 6, 7, 8, 9, and 10 for accessing the tourniquet system 100 but could include more or less flaps and tourniquets. The flaps are releasable secured to the garment by hook and loop fasters or other suitable quick release connectors. Flaps 3 and 5 are located such that the tourniquet band 44 of the tourniquet system 100 is centered proximate the level of superior position of the bicep. Flaps 6 and flap 4 are located such that the tourniquet band 44 of tourniquet system 100 is centered approximately two centimeters below the elbow of the wearer. Flaps 8 and 7 are located such that the tourniquet band 44 of tourniquet system 100 is centered approximately two centimeters distal to the inguinal crease and flaps 9 and 10 are located such that the tourniquet band 44 of tourniquet system 100 is centered approximately two centimeters distal to the tibial tuberosity.

Figure 2:
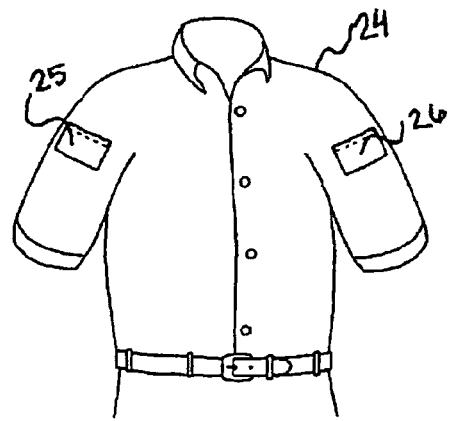
FIG. 2 shows a perspective view disclosing the tourniquet system-equipped short-sleeved shirt formed in accordance with the present invention.

FIG. 2 discloses an alternate embodiment of the current invention illustrated in a garment that includes a short-sleeved, button-down shirt 24 with flap 25 and flap 26 for accessing the tourniquet system 100. Flaps 25 and 26 are located such that the tourniquet band 44 of the tourniquet system 100 is centered proximate the level of superior position of the bicep.

Figure 3:
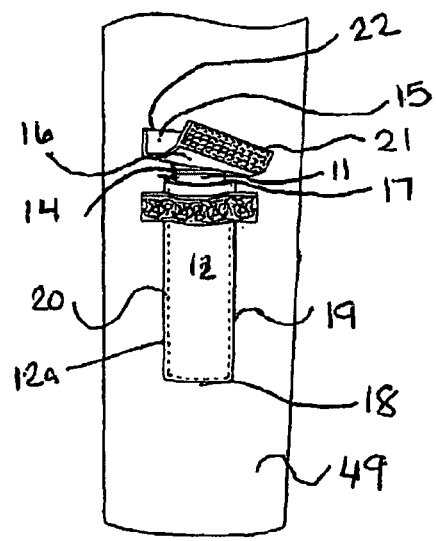
FIG. 3 shows a vertical sectional view disclosing a suggested location for the storage location of the lever or bar.
Figure 14:
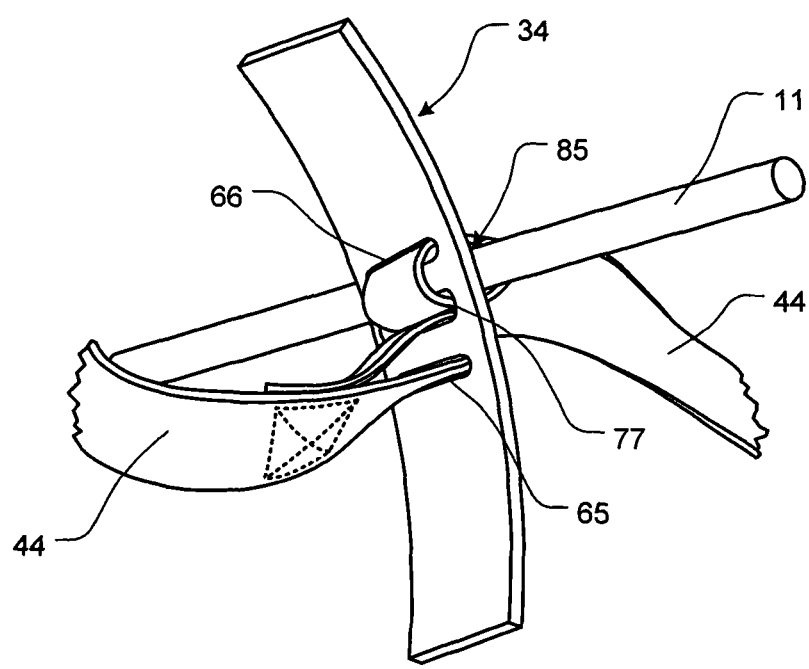
FIG. 14 shows a perspective view of an exemplary embodiment of a tourniquet system according to this invention, wherein an optional step in the application of the tourniquet system is illustrated.

FIG. 3 discloses a suggested location and orientation for a storage location of the optional lever or bar 11 on the outer surface 49 of the garment during times when it is not employed to further assist in tightening a tourniquet 23, as illustrated in FIG. 14. The storage comprising of a generally rectangular webbing member 12*a* sown or otherwise secured to the other surface 49 of the garment and having an outer surface 12 and an inner surface 14, an upper edge 17, a lower edge 18, a right edge 19 and a left edge 20. The inner surface 14 of the webbing secured to the outer surface 49 of the garment at the lower edge 17, the right edge 19 and the left edge 20 in any suitable manner such that a channel is formed of the same size or slightly larger than the lever or bar 11 and leaving unsecured the upper edge 17 for insertion of the lever or bar 11 and storage during times of non-use. The webbing having a flap with outer surface 15 and inner surface 16, a lower edge 21 and an upper edge 22. The inner surface 16 secured to the outer surface 49 of the garment at the upper edge 22 in any suitable manner such that the lower edge 21 of the inner surface 16 of the flap overlaps the upper edge 17 of the outer surface 12 of the webbing. At the point of overlap, the lower edge 21 of the inner surface 16 of the flap and the upper edge 17 of the outer surface 12 of the webbing, having a securing means, such as convention hook and loop fasteners or other suitable quick release connection, to secure the lever or bar 11 in the storage location.

Figure 4:
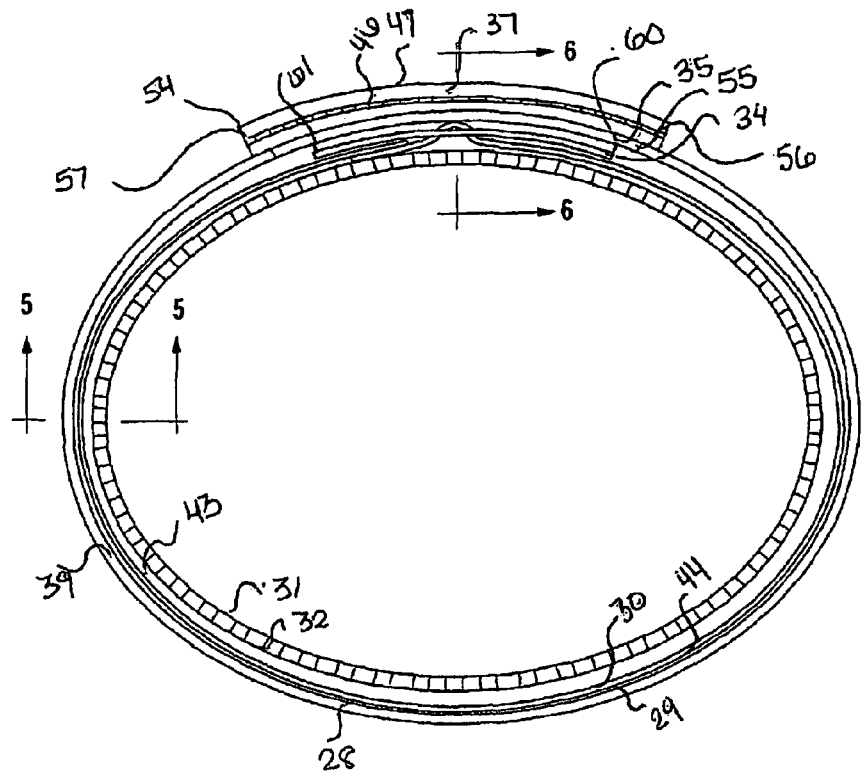
FIG. 4 shows a cross section of one particular embodiment of the tourniquet system formed in accordance with the present invention.

FIG. 4 discloses a horizontal cross section of an exemplary embodiment of the tourniquet system 100. The innermost continuous ring is the webbing or band 40, which has an outer surface 31 and an inner surface 32. The webbing 40 has an upper edge 41, see FIG. 6, and a lower edge 42. The fabric of the garment has an inner surface 28. The inner surface of the webbing 32 is secured at the upper edge 41 and the lower edge 42 to the inner surface of the garment 28 in any suitable manner that may include sewing or adhering or molding such that a channel 43 is formed of a slightly larger than the tourniquet band 44 and continuing the entire circumference of the inner surface of the garment 28. The tourniquet band 44, with outer surface 29 and inner surface 30, is located within the channel 43 in such a manner that the outer surface of the webbing 31 is adjacent but would not noticeably impede the movement of the inner surface 30 of the tourniquet band 44 such that when the tourniquet is tightened or loosened, the tourniquet band 44 is free to move within the channel 43.

The channel makes the tourniquet more comfortable and less noticeable but does not interfere with the use of the tourniquet. In the same manner, the outer surface 29 of the tourniquet band 44 is adjacent to the inner surface of the fabric of the garment 28 wherein the inner surface of the garment 28 does not noticeably impede the movement of the outer surface 29 of the tourniquet band 44.

The tourniquet 23 has a tightening and securing mechanism 34 located such that the outer surface 29 of the tourniquet band 44 lies beneath and loops through the tightening and securing mechanism 34 in a manner that allows for the circumference of the tourniquet band 44 to be decreased in diameter thus producing a higher radial pressure on the extremity to staunch any current blood flow and allows for the decreased circumference to be maintained without constant torque from an outside source. The width of the tightening and securing mechanism 34 is defined as the distance between the right edge 60 of the tightening and securing mechanism 34 and the left edge 61 of the tightening and securing mechanism 34. The tightening and securing mechanism 34 lies beneath a portal 35 in the garment 39 through which the tourniquet system 100 can be accessed.

The tightening and securing mechanism 44 extends from a first end to a second end and is of a sufficient length to allow a user to acquire a sufficient purchase on the tightening and securing mechanism 44 to effectively rotate the tightening and securing mechanism and create a sufficient tourniquet force.

The portal has an upper edge 53 (See FIG. 6.), a lower edge 52 (See FIG. 6.), a left edge 55 and a right edge 54. The distance between the left edge 55 and the right edge 54 of the portal can be as large as or larger than the width of the tightening and securing mechanism 34. The portal 35 is protected by a flap 37 with inner surface 46 and outer surface 47 an upper edge 58 (See FIG. 6.), a lower edge 59 (See FIG. 6.), a right edge 56 and left edge 57. The flap inner surface 46 overlaps with the outer surface of the garment 49 below the lower edge of the portal 52 (See FIG. 6.) and the flap left edge 57 and flap right edge 56 overlap the left edge 56 and right edge 57 of the portal, respectively. At the point of overlap of the lower edge of the inner surface 46 of the flap with the outer surface of the garment 49 there is a temporary securing means 51 (such as a hook and loop fastener) to secure the flap 37 and protect the tourniquet system 100 when not in use and to allow quick access when tourniquet use is required.

Figure 5:
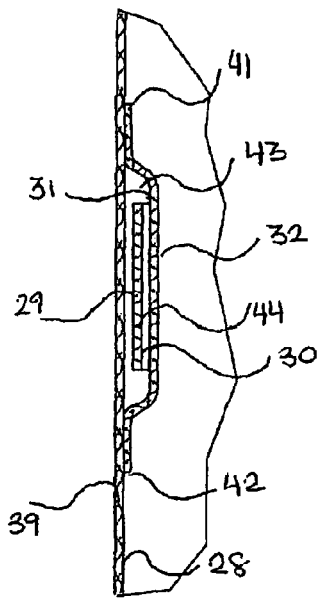
FIG. 5 shows a cross section of one particular embodiment of the tourniquet system's channel formed in accordance with the present invention.

FIG. 5 discloses a vertical sectional view of the channel 43 taken along line 5-5 of FIG. 4 where the tourniquet band 44 is located internal to the garment 39. The webbing 40 has an upper edge 41 a lower edge 42 an inner surface 32 and an outer surface 31. The inner surface of the webbing 32 is secured at the upper edge 41 and the lower edge 42 to the inner surface of the garment 39 in any suitable manner such that a channel 43 is formed of the same size or slightly larger than the tourniquet band 44 and continuing the entire circumference of the inner surface of the garment 28.

The tourniquet band 44, with outer surface 29 and inner surface 30 is located within the channel 43 in such a manner that the outer surface of the webbing 31 is adjacent but in no way would noticeably impede the movement of, the inner surface 30 of the tourniquet band 44 such that when the tourniquet is tightened or loosened, it is free to move within the channel 43. In the same manner, the outer surface 29 of the tourniquet band 44 is adjacent to the inner surface of the fabric of the garment 28 wherein the inner surface of the garment 28 in no way impedes, in any noticeable manner, the movement of the outer surface 29 of the tourniquet band 44 while at the same time the webbing 40 and the fabric of the garment 39 are means of protecting the integrity of the tourniquet band 44 positioning the tourniquet band 44 within the garment.

Figure 6:
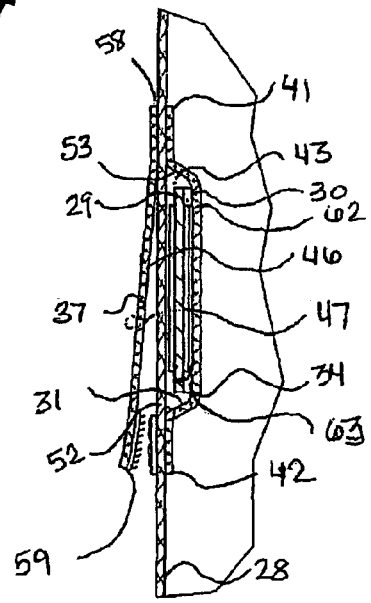
FIG. 6 shows a cross section of one particular embodiment of the tourniquet system's channel formed in accordance with the present invention.

FIG. 6 discloses a vertical sectional view of the flap 37 taken along line 6-6 of FIG. 4 which overlays and protects the tourniquet tightening and securing mechanism 34 accessible through the portal 35. The webbing 40 is connected to the garment 28 in the same manner as that described in FIG. 5. Except FIG. 6 discloses the tightening and securing mechanism 34 located such that the outer surface of the tourniquet band 44 lies beneath and loops through the tightening and securing mechanism 34 in the manner described in FIG. 4. The distance between the upper edge 53 and lower edge 52 of the portal can be a large or larger than the height of the tightening and securing mechanism 34. The height of the tightening and securing mechanism 34 is defined as the distance between the upper edge 62 of the tightening and securing mechanism 34 and the lower edge 63 of the tightening and securing mechanism 34. The portal 35 is protected by a flap 37 with inner surface 46 and outer surface 47 an upper edge 58 and lower edge 59. The inner surface of the flap 46 is secured to the outer surface of the garment 49 at the upper edge 53 in any suitable manner such that the lower edge 59 of the inner surface 46 of the flap overlaps the lower edge of the portal 52 and lies adjacent to the outer surface of the garment 49. At the point of overlap, the lower edge 59 of the inner surface 46 of the flap and the outer surface of the garment 49 have a temporary securing means, such as a hook and loop fastener to secure the flap 37 when the invention is not in use and allow easy access to the tightening and securing mechanism 34 when needed.

The tourniquet system of the invention can be applied with one hand. This is made possible by the mounting of the tourniquet in the garment in the correct location and making it accessible with one hand and making it possible for a person to tighten with one hand to stem blood flow. When the tourniquet is not secured on the clothing, it may be difficult to attach, apply, and tighten the loose tourniquet with only one hand.

Figure 7:
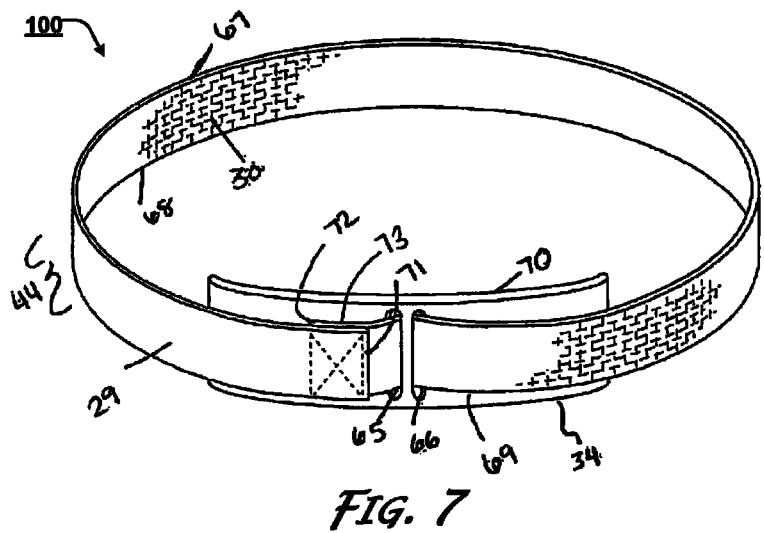
FIG. 7 shows a perspective view of one embodiment of the tourniquet tightening and securing mechanism in its secured position.

FIG. 7 discloses another embodiment of a tourniquet of the current invention wherein the tightening and securing mechanism 34 attached to the tourniquet band 44 contains two apertures 65 and 66. The height of the apertures 65 and 66 is defined by the distance between the upper edge 67 of the tourniquet band 44 and the lower edge 68 of the tourniquet band 44. The apertures 65 and 66 must be high enough to allow the tourniquet upper edge 67 and lower edge 68 to be accepted. In the same manner, the width of the apertures 65 and 66 is defined by the distance between the inner surface 30 and outer surface 29. The apertures must be wide enough to allow the inner surface 30 and outer surface 29 of the tourniquet band 44 to pass through with no noticeable resistance. The distance between the upper edge 62 and lower edge 63 of the tourniquet tightening and securing mechanism 34 must only be slightly larger than the height of the apertures 65 and 66.

Generally, the apertures 65 and 66 are formed proximate a center of the tightening and securing mechanism 34.

In various exemplary embodiments, the tightening and securing mechanism 34 is formed of a rigid or a semi-rigid plastic or polymeric material, such as a polymeric composite. In various exemplary embodiments, the tightening and securing mechanism 34 is injection-molded. Alternatively, the tightening and securing mechanism 34 may be heat-formed from sheet stock, such as, for example a polymer. In still other exemplary embodiments, the tightening and securing mechanism 34 may be stamped or rolled from a sheet of metal or may be formed from aluminum, titanium, and/or other metals, as well as various alloys and composites thereof, glass-hardened polymers, polymer or fiber reinforced metals, carbon fiber or glass fiber composites, continuous fibers in combination with thermoset and thermoplastic resins, chopped glass or carbon fibers used for injection molding compounds, laminate glass or carbon fiber, epoxy laminates, woven glass fiber laminates, impregnate fibers, polyester resins, epoxy resins, phenolic resins, polyimide resins, cyanate resins, high-strength plastics, nylon, glass or polymer fiber reinforced plastics, thermoform and/or thermoset sheet materials, and/or various combinations of the foregoing. It should also be appreciated that the tightening and securing mechanism 34 may be formed of, over-molded, or coated by multiple materials. Thus, it should be understood that the material or materials used to form the tightening and securing mechanism 34 is a design choice based on the desired appearance, flexibility, and functionality of the tightening and securing mechanism 34.

As illustrated in FIG. 7, the inner surface 30 of the exemplary tourniquet band 44 lies adjacent to the outer surface 69 of the tightening and securing mechanism 34 until opening 66. The tourniquet band 44 is then passed through opening 66 such that the outer surface of the band 29 is adjacent to the inner surface 70 of the tightening and securing mechanism 34. The tourniquet band 44 is then passed through opening 65 such that the bands inner surface 30 is again adjacent to the outer surface 69 of the tightening and securing mechanism 34. The left edge 71 and right edge 72 of the tourniquet band 44 are arranged such that a significant amount of the inner surface 30 of the tourniquet at the left edge 71 overlaps the outer surface 29 of the tourniquet at the right edge 72. At the point of overlap a temporary securing means 73 (such as a hook and loop fastener) is used to close the tourniquet band 44 when not in use and to release, tighten and re-secure when in use.

Figure 8:
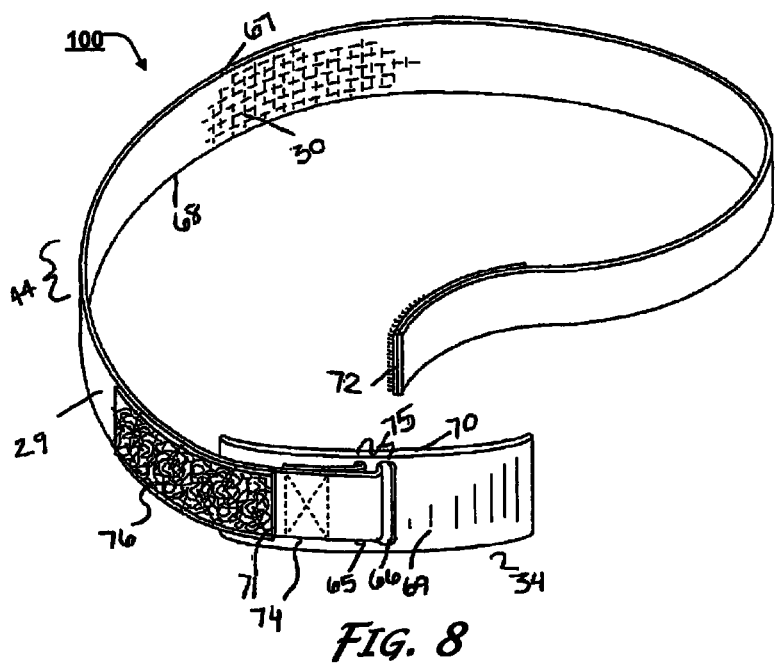
FIG. 8 shows a perspective view of an exemplary embodiment of the tourniquet tightening and securing mechanism in its unsecured position.

FIG. 8 discloses another embodiment of the tourniquet of the current invention. The tightening and securing mechanism 34 is formed in the same manner; however, the tourniquet band 44 is arranged in a different configuration. In this embodiment, the left edge 71 of the tourniquet band 44 is passed through opening 66 such that the inner surface of the band 30 is adjacent to the inner surface 70 of the tightening and securing mechanism 34. The left edge 71 is then passed through opening 65 such that the inner surface 30 of the left edge 71 of the band is now adjacent to a portion of the inner surface of the band 30 farther from the left edge 74. At this point, the tourniquet band 44 is secured to itself in any suitable manner such that a loop 75 is formed near the left edge 71 of the tourniquet wherein the tightening and securing mechanism 34 is contained within the loop 75.

The outer surface 29 of the tourniquet band 44 adjacent to the point where the tourniquet is secured to itself 74 contains one end of a temporary securing means 76 (such as a hook and loop fastener). Along the inner surface 30 of the tourniquet band 44 near the right edge 72 lies the matching end of the temporary securing means such that the right edge is passed through the tightening and securing mechanism opening 66 in a manner that before passing through the right edge 72 outer surface 29 is adjacent to the inner surface 70 of the tightening and securing mechanism 34 and after passing through the inner surface 30 of the right edge 72 overlaps the temporary securing means 76 such that the temporary securing means may be used to tighten, secure, release and re-secure the tourniquet as needed.

Figure 9:
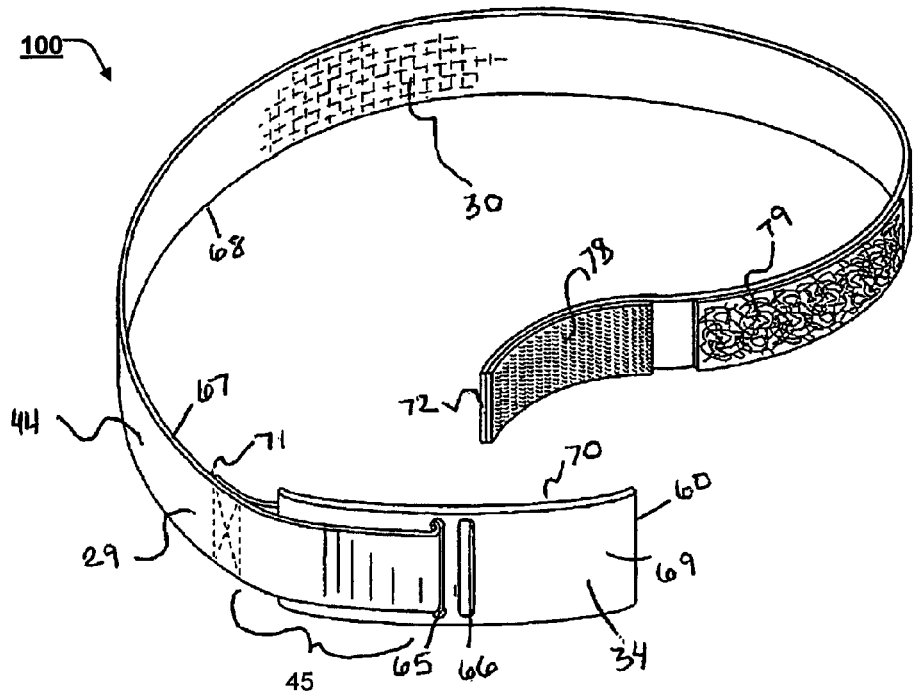
FIG. 9 shows a perspective view of one embodiment of the tourniquet tightening and securing mechanism in its unsecured position.

FIG. 9 discloses another exemplary embodiment of a tourniquet system 100 of the current invention wherein on tightening and securing mechanism 34 is formed in the same manner as FIGS. 7 and 8. However, the tourniquet band 44 is affixed to the mechanism 34 in a differing manner. In this embodiment, the inner surface 30 of the left edge 71 is passed over the outer surface 69 of the mechanism. The left edge 71 is then passed through opening 65 in a manner such that the inner surface 30 of the left edge 71 then becomes adjacent to the inner surface 70 of the mechanism until it meets and overlaps another portion of the inner surface 30 of the band. At the point of overlap the inner surfaces are secured to each other in any suitable manner such that a loop 45 is formed containing wholly half of the tightening and securing mechanism 34.

Near the outer surface 29 of the right edge 72 of the tourniquet band 44 lie two opposing ends of a temporary securing system (such as A hook and loop fastener) 78 and 79. The tourniquet is activated by passing the right edge 72 of the band through the opening 66 such that after passing through opening 66 the outer surface 69 of the right edge 72 adjacent to the outer surface 69 of the tightening and securing mechanism 34. The outer surface 29 of the right edge 72 should pass beyond the right edge 60 of the tightening and securing mechanism 34 and overlap the outer surface of the band 29 where the opposing temporary securing means 79 is located in order to secure the tourniquet when needed.

Figure 10:
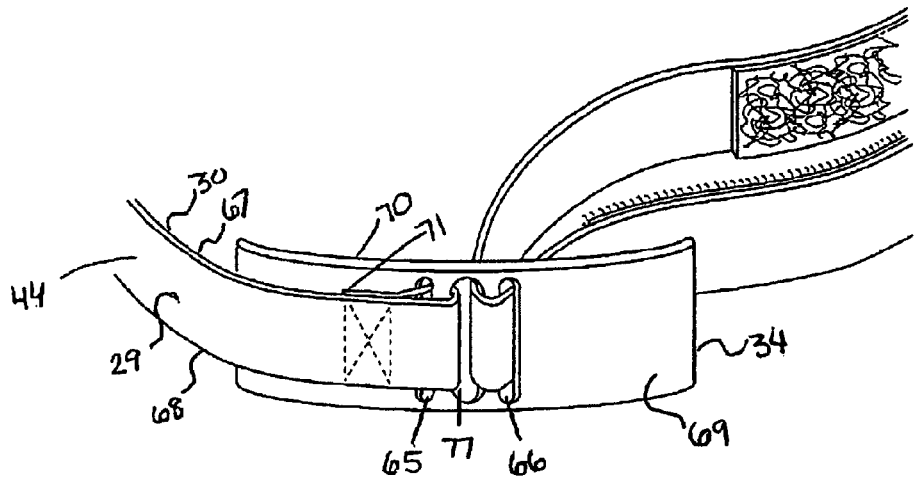
FIG. 10 shows a perspective view of another embodiment of the tourniquet tightening and securing mechanism in its unsecured position.

FIG. 10 discloses yet another embodiment of the tightening and securing mechanism 34 of the current invention. The mechanism is formed in the same manner as noted in FIGS. 7-9. However, an additional opening 77 in between apertures 65 and 66 with the same height as those in FIGS. 7-9 is present. Opening 77 must have a width at least as great as twice the distance between the inner surface 30 and outer surface 29 of the tourniquet band 44 and must allow two tourniquet bands 44 to pass through at the same time with no noticeable resistance. Loop 75 as in FIG. 7 is again created using apertures 65 and 77. However, the right edge 72 (See FIG. 8.) of the tourniquet band 44 is passed through opening 77 such that the outer surface 29 of the right edge 72 is adjacent to the outer surface 69 of the tightening and securing mechanism 34. The right edge 72 is then passed through opening 66 such that the outer surface 29 of the tourniquet band 44 is now adjacent to itself and the inner surface 30 of the tourniquet band 44 is adjacent to the inner surface 70 of the tightening and securing mechanism 34. Placed upon the overlap of the outer surface 29 of the right edge 72 of the tourniquet band 44 before and after the band has been threaded through the apertures 77 and 66 is a temporary securing means 78 and 79 such that the overlap may be tightened, secured, and released when needed.

The use of the tourniquet system of the invention would be as follows. If an appendage of a wearer of the garment was injured and a tourniquet force was needed to stop bleeding the medic or person treating the injured wearer would simply lift the flap 7 to expose the tourniquet band 44. The medic would then apply tourniquet pressure to the tourniquet band 44 to stop the blood loss. The type of pressure applied would be the same as with other standard tourniquets based on the need of the patient.

Figure 11:
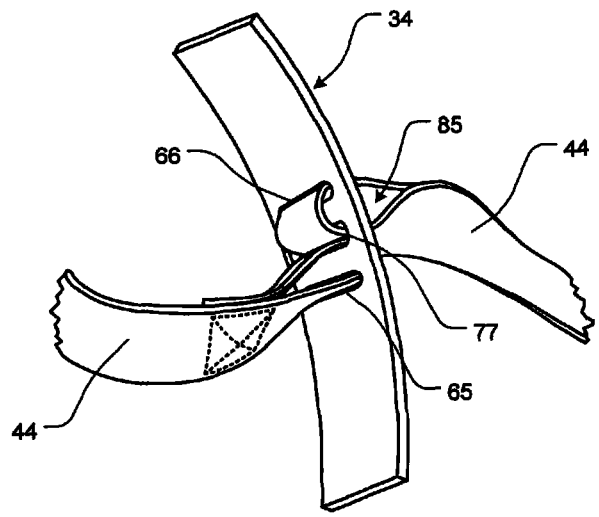
FIG. 11 shows a perspective view of an exemplary embodiment of a tourniquet system according to this invention, wherein an initial step in the application of the tourniquet system is illustrated.
Figure 12:
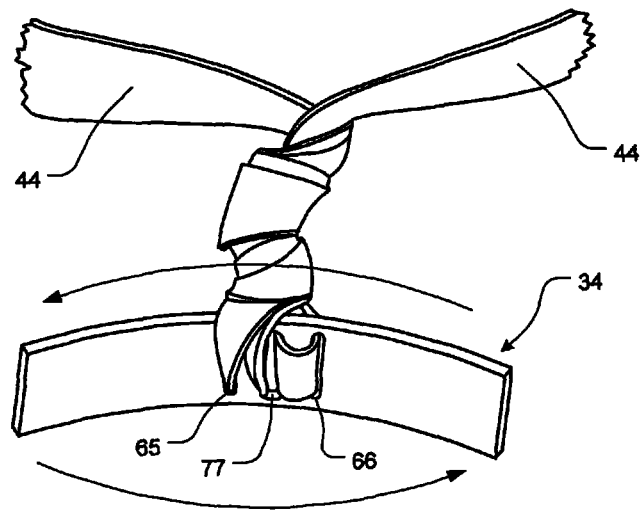
FIG. 12 shows a perspective view of an exemplary embodiment of a tourniquet system according to this invention, wherein a subsequent step in the application of the tourniquet system is illustrated.
Figure 13:
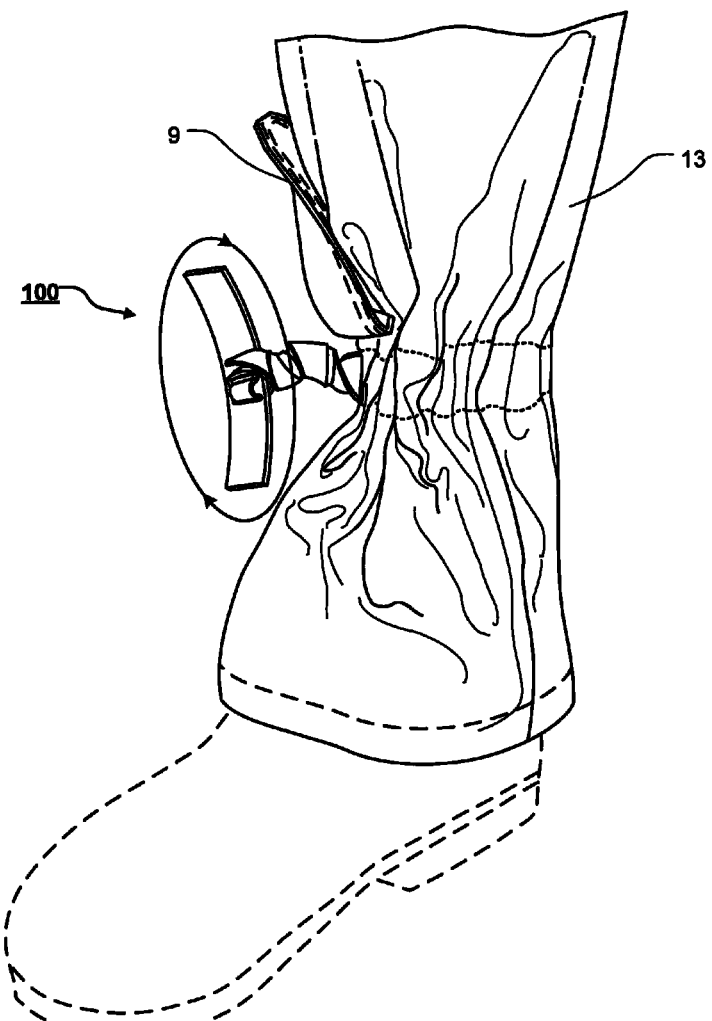
FIG. 13 shows exemplary utilization of an exemplary embodiment of a tourniquet system incorporated into a pair of pants, according to this invention.

FIGS. 11-13 illustrate the application of the exemplary tourniquet system 100. In its unused position, the curvature of the tightening and securing mechanism 34 substantially follows the curvature of the user's appendage or the garment. When the tourniquet system is in use, the orientation of the tightening and securing mechanism 34 is altered such that the curvature of the tightening and securing mechanism 34 tends to curve the tightening and securing mechanism 34 away from the curvature of the extremity where the tightening and securing mechanism 34 is positioned, thus allowing the tightening and securing mechanism 34 to not interfere with the limb when used and to be more easily manipulated by the operator. Alternatively, the tightening and securing mechanism 34 may be substantially planar over its length.

As illustrated in FIGS. 11-13, when in use, the tightening and securing mechanism 34 is flipped over and repositioned such that the curvature of the tightening and securing mechanism 34 is opposite the curvature of the user's appendage or garment.

Once the tightening and securing mechanism 34 is repositioned, the tightening and securing mechanism 34 is rotated or turned, as illustrated in FIGS. 12 and 13. As the tightening and securing mechanism 34 is rotated or turned, the slack of the tourniquet band 44 is taken up as the material of the tourniquet band 44 is twisted together and the tourniquet band 44 is tightened around the extremity to create pressure. As the tightening and securing mechanism 34 continues to be twisted, additional pressure is created by the tourniquet band 44.

FIG. 13 shows exemplary utilization of an exemplary embodiment of the tourniquet system 100 incorporated into a pair of pants 13, according to this invention. It should be appreciated that the pants 13 are merely for exemplary purposes and the pants 13 could be of other types. As illustrated in FIG. 13, during use of the tourniquet system 100, the flap 9 is separated from the main body of the pants 13 and lifted to allow access to the tourniquet system 100. Once access to the tourniquet system 100 is obtained, the tourniquet system 100 may be applied and/or released as described herein.

FIG. 14 shows a perspective view of an exemplary embodiment of a tourniquet system 100, wherein an optional step in the application of the tourniquet system is illustrated. As illustrated in FIG. 14, the lever or bar 11 may be inserted within a loop 85 formed in the tourniquet band 44 to provide additional leverage when utilizing the tourniquet system 100 and twisted in an effort to tighten the tourniquet band 44 to an even further degree.

If the lever or bar 11 is needed, the flap 15 could be released to expose the bar 11. The bar 11 could be removed from the pouch 12 and inserted in the loop 85 and twisted to apply additional pressure. Once the tourniquet band 44 is tightened to the desired degree, the lever or bar 11 may then be removed from the loop 85 and returned to the pouch 12.

While this invention has been described in conjunction with the exemplary embodiments outlined above, it is evident that many alternatives, modifications, variations, and equivalents will be apparent to those skilled in the art, which can be reasonably included within the spirit and scope of the foregoing description.

Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A tourniquet system, consisting of:
    at least one circumferential enclosed channel formed in a garment;
    a tourniquet band positioned in said at least one circumferential enclosed channel;
    a tightening and securing mechanism associated with said tourniquet band, wherein said tightening and securing mechanism consists of an elongate portion of material having at least two apertures formed therethrough, and wherein at least a portion of said tourniquet band passes through at least one of said at least two apertures of said tightening and securing mechanism, such that when said tightening and securing mechanism is turned, a diameter of said tourniquet band is decreased and a tourniquet force is applied to an inside wall of said circumferential enclosed channel; and
    at least one portal in said garment, proximate said circumferential enclosed channel, to provide access to said tightening and securing mechanism.

2. The tourniquet system of claim 1, wherein said tightening and securing mechanism is substantially curved over its length.

3. The tourniquet system of claim 1, wherein said tightening and securing mechanism is substantially planar over its length.

4. The tourniquet system of claim 1, wherein said tightening and securing mechanism extends from a first end to a second end.

5. The tourniquet system of claim 1, wherein said tightening and securing mechanism is of a sufficient length to allow a user to acquire an appropriate purchase on said tightening and securing mechanism to rotate said tightening and securing mechanism to create an effective tourniquet force.

6. The tourniquet system of claim 1, wherein said at least two apertures are formed proximate a center of said tightening and securing mechanism.

7. The tourniquet system of claim 1, wherein portions of said tourniquet band are permanently joined to form a continuous tourniquet band.

8. The tourniquet system of claim 1, wherein portions of said tourniquet band are releasably joined to form a continuous tourniquet band.

9. A tourniquet system, consisting of:
- at least one circumferential enclosed channel formed in a garment;
- a tourniquet band positioned in said at least one circumferential enclosed channel;
- a tightening and securing mechanism associated with said tourniquet band, wherein said tightening and securing mechanism consists of an elongate portion of material having at least two apertures formed therethrough, and wherein a first end portion of said tourniquet band passes through at least one of said apertures of said tightening and securing mechanism and is permanently joined to a portion of said tourniquet band and a second end portion of said tourniquet band passes through at least one of said apertures of said tightening and securing mechanism and is permanently joined to a portion of said tourniquet band; such that when said tightening and securing mechanism is turned, a diameter of said tourniquet band is decreased and a tourniquet force is applied to an inside wall of said circumferential enclosed channel; and
- at least one portal in said garment, proximate said circumferential enclosed channel, to provide access to said tightening and securing mechanism.

10. The tourniquet system of claim 9, wherein said tightening and securing mechanism is substantially curved over its length.

11. The tourniquet system of claim 9, wherein said tightening and securing mechanism is substantially planar over its length.

12. The tourniquet system of claim 9, wherein said tightening and securing mechanism extends from a first end to a second end.

13. The tourniquet system of claim 9, wherein said at least two apertures are formed proximate a center of said tightening and securing mechanism.

14. A tourniquet system, consisting of:
- a tourniquet band; and
- a tightening and securing mechanism associated with said tourniquet band, wherein said tightening and securing mechanism consists of an elongate portion of material having at least two apertures formed therethrough, and wherein at least a portion of said tourniquet band passes through each of said at least two apertures of said tightening and securing mechanism, such that when said tightening and securing mechanism is turned, a diameter of said tourniquet band is decreased.

* * * * *